United States Patent [19]
Helderman

[11] Patent Number: 5,371,189
[45] Date of Patent: Dec. 6, 1994

[54] MONOCYTE-DERIVED INSULIN RECEPTOR REGULATORY FACTOR

[75] Inventor: J. Harold Helderman, Nashville, Tenn.

[73] Assignee: Vanderbilt University, Nashville, Tenn.

[21] Appl. No.: 57,161

[22] Filed: Apr. 30, 1993

[51] Int. Cl.$^5$ .............................................. C07K 13/00
[52] U.S. Cl. .................................. 530/350; 435/69.1; 530/303
[58] Field of Search ................ 435/69.1; 530/350, 412, 530/303

[56] References Cited

PUBLICATIONS

Helderman et al., Cytokine, vol. 4, 528-36, 1992.
Koffler M. et al. "Immunobiological consequence of regulation of insulin receptor on alloactivated lymphocytes in normal and obese subjects," Diabetes, 40:364-370 (Mar. 1991).
Matsushima K. et al., "Purification and characterization of a novel monocyte chemotactic and activating factor produced by a human myelomonocytc cell line," J. Exp Med, 169:1485-1490 (Apr. 1989).
Matsushima K. et al., "Molecular cloning of a human monocyte-derived neutrophil chemotactic factor (MDNCF) and the induction of MDNCF mRNA by interleukin 1 and tumor necrosis factor," J. Exp Med, 167:1883-1893 (Jun. 1988).
Ercolani L. et al., "Tunicamycin blocks the emergence and maintenance of insulin receptors on mitogen-activated human T-lymphocytes," Metabolism, 33:309-316 (Apr. 1984).
Helderman J. H. et al., "Effect of insulin and transferrin in the maitenance of the activated state of the T-lymphocyte induced by alloantigen," Diabetalogia, 27:99-101 (1984).
Helderman J. H. et al., "The role of insulin in the intermediary metabolism of the activated thymic derived lymphocyte," J Clin Invest, 67:1636-1642 (Jun. 1981).
Spira, G. et al., "Cell-surface immunoglobulin and insulin receptor expression in an EBV-negative lymphoma cell line and its EBV-converted sublines," The Journal of Immunology, 126(1):122-126 (Jan. 1981).
Strom T. B. et al., "Comparison of ligand specific rat allosensitized lymphocyte insulin receptors as assessed in binding and functional (lymphocyte mediated cytotoxicity) assays," Cell Immunol, 53:382-388 (1980).
Helderman J. H. et al., "A close relationship between cytotoxic T lymphocytes generated in the mixed lymphocyte culture and insulin receptor bearing lymphocytes: enrichment by density gradient centrifugation," Cell Immunol, 46:247-258 (1979).
Helderman J. H. et al., "Role of protein and RNA synthesis in the developement of insulin binding sites on activated thymus-derived lymphocytes," J Biol Chem, 254(15):7203-7207 (1979).
Helderman J. H. et al., "The insulin receptor as a universal marker of activated lymphocytes," Eur J Immunol, 8:589-595 (1978).
Helderman J. H. et al., "Specific insulin binding site on T and B lymphocytes as a marker of cell activation," Nature (London) 274:62-63 (Jul. 6, 1978).
Helderman J. H. et al., "Emergence of insulin receptors upon alloimmune T cells in the rat," J Clin Invest, 59:338-344 (Feb. 1977).
Koren H. S. et al., "Identification of macrophage-like characteristics in a cultured murine tumor line," J Immunol, 114:894-897 (Feb. 1975).

Primary Examiner—Garnette D. Draper
Assistant Examiner—Sally Teng
Attorney, Agent, or Firm—Needle & Rosenberg

[57] ABSTRACT

The present invention relates to a purified monocyte-derived insulin receptor regulatory factor, which has the biological activity of reducing insulin receptor binding on T-lymphocytes. Additionally, the invention relates to a nucleic acid that codes for the monocyte-derived insulin receptor regulatory factor, a recombinant protein produced therefrom, and an antibody to the factor. The present invention also relates to a method of reducing insulin receptor binding on activated T-lymphocytes, including administration of the protein to a subject.

2 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Homo sapiens
        ( G ) CELL TYPE: Monocyte
        ( H ) CELL LINE: THP-1 (ATCC Accession No.: TIB 202)

( i x ) FEATURE:
        ( A ) NAME/KEY: Modified-site
        ( B ) LOCATION: 17..19
        ( D ) OTHER INFORMATION: /label=AminoAcid18
            / note="Amino acid at position 18 is either
            proline (Pro) or lysine (Lys)."

( i x ) FEATURE:
        ( A ) NAME/KEY: Modified-site
        ( B ) LOCATION: 20..22
        ( D ) OTHER INFORMATION: /label=Aminoacid21
            / note="Amino acid at position 21 is either
            threonine (Thr) or isoleucine (Ile)."

( i x ) FEATURE:
        ( A ) NAME/KEY: Modified-site
        ( B ) LOCATION: 21..23
        ( D ) OTHER INFORMATION: /label=AminoAcid22
            / note="Amino acid at position 22 is either valine
        ( V a l ) or glutamic acid (Glu)."

( x i ) SEQUENCE DESCRIPTION: SEQ ID NO:1:

```
Asp Ser Val Gly Ala Gly Glu Pro Lys Leu Tyr Xaa Xaa Xaa Asp Val
1               5                   10                  15

Asp Xaa Ser Ala Xaa Xaa Ser
            20
```

( 2 ) INFORMATION FOR SEQ ID NO:2:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Mouse
        ( F ) TISSUE TYPE: Monocyte
        ( G ) CELL TYPE: P388D1 (ATCC Accession No. TIB 63)

( x i ) SEQUENCE DESCRIPTION: SEQ ID NO:2:

```
Xaa Gly Val Gly Ala Gly Glu Pro Lys Leu Pro Leu Met Val Lys Asp
 1               5                   10                  15
    Leu Asp Ala Val Arg Xaa Xaa Pro Ala Ala
                20                  25
```

MONOCYTE-DERIVED INSULIN RECEPTOR REGULATORY FACTOR

ACKNOWLEDGEMENTS

This invention was made in part with government support under Grant AM22150 awarded by the National Institutes of Health. The government has certain rights in the invention.

BACKGROUND OF THE INVENTION

1. Field of the Invention

The instant invention relates to a novel cytokine. In particular, a purified monocyte derived insulin receptor regulatory factor, which has a biological activity of reducing insulin receptor binding on T-lymphocytes, is provided and characterized. Additionally, provided are methods of altering insulin receptor binding on T-lymphocytes.

2. Background Art

The insulin receptor is a non-constitutive membrane bound heterodimer found on the lymphocyte surface which is a marker of lymphocyte activation by antigen or lectin (1–3), indicates the ontogenetic state of that cell (14), and is the vehicle by which the growth factor insulin subserves its immunobiologic roles (1,4–7). We have demonstrated that regulation of the insulin receptor itself is the means by which the lymphocyte is variously responsive to ambient levels of the hormone insulin which is under separate, non-immunologically mediated control (15). The means by which the insulin receptor is regulated, then, becomes important in understanding lymphocyte responsiveness to hormonal manipulations.

We recently have characterized three distinct mechanisms for such regulation: 1) the provision of a signal to initiate reading of the insulin receptor gene sequence (1,13); 2) the regulation of the number of copies of receptors once synthesized by binding of the ligand to its receptor and internalization of the ligand-receptor complex (16); 3) alteration in the number of copies of receptor molecules synthesized as a function of ambient insulin as signaled by monocytes (7,10,11,17). The latter mechanism is unique to the immune system, resembles the cell-cell interaction by which Antigen Presenting Cells (APC) cooperate with T-lymphocytes for the presentation of such environmental signals as antigen, and cannot involve ligand binding since the monocyte-derived signals are provided at a time when lymphocytes are insulin receptor negative.

Knowledge of the regulation of the insulin receptor on activated lymphocytes permits a fuller understanding of the means by which insulin subserves its signal function with respect to the lymphocyte activation cascade. There thus exists a need to isolate and characterize regulators of the insulin receptor and to study their biological activity. This invention satisfies this need by providing a purified regulator of the insulin receptor.

SUMMARY OF THE INVENTION

The present invention relates to a purified monocyte-derived insulin receptor regulatory factor, which has the biological activity of reducing insulin receptor binding on T-lymphocytes.

The invention further relates to a nucleic acid that codes for the monocyte-derived insulin receptor regulatory factor, a recombinant protein produced therefrom, and an antibody to the factor.

The present invention also relates to a method of reducing insulin receptor binding on activated T-lymphocytes, including administration of the factor to a subject.

The instant invention further relates to a method of inhibiting the biological activity of monocyte-derived insulin receptor regulatory factor.

The invention also relates to a method of diminishing the cytotoxic effect of cytotoxic T-cells.

Accordingly, it is an object of the present invention to provide a purified monocyte-derived insulin receptor regulatory factor, a nucleic acid encoding such factor, and an antibody selectively reactive with such factor.

Another object of the present invention is to provide methods of utilizing the monocyte-derived insulin receptor regulatory factor to reduce insulin receptor binding on T-lymphocytes and to diminish the cytotoxic effect of cytotoxic T-lymphocytes, and methods of inhibiting the same.

DESCRIPTION OF THE PREFERRED EMBODIMENTS

The present invention may be understood more readily by reference to the following detailed description of specific embodiments and the Examples and Figures included therein.

The invention provides the characterizion and purification to homogeneity of a novel monocyte-derived polypeptide with an important inhibitory function. This material has an unique hitherto undescribed effect. It inhibits T-lymphocyte generation of the non-constitutive, T-lymphocyte insulin receptor molecule in response to lectin or antigen which would diminish the capacity of the ligand, insulin, to enhance certain immunologic activities such as the function of cytotoxic T-cells (1). The cell of origin is lymphocytic, the function is coordinate with Interleukin-2 and provides another positively directed signal. The protein of this invention provides a counter-balancing force to Interleukin-12, is monocyte derived, would diminish cytotoxic T-cell responses as a function of growth factor in the ambient environment.

As used in the claims, "a" can mean one or more.

As used herein, a "purified" protein is one that has been purified substantially to homogeneity, and thus is essentially free of cell components with which the protein is normally associated.

As used herein, "monocyte-derived insulin receptor regulatory factor," or "MIRRF" refers to a protein which is produced and secreted by monocytes and functions, at least in part to reduce insulin binding to the insulin receptor of T-lymphocytes. MIRRF is between 14 and 21 kDa, and it is exemplified by the amino acid sequences of SEQ ID NO. 1 and SEQ ID NO. 2. It should be understood however that sequencing errors could occur. Such errors can be determined by repeating procedures utilized herein or recognized in the art. It is also apparent that certain amino acids can be substituted, added or deleted which would not adversely affect the activity. Such modifications are within the scope of the invention.

A protein "having the biological activity of reducing insulin receptor binding on T-lymphocytes" means that it produces a decrease in insulin binding to the insulin receptor of T-lymphocytes as assayed by the bioassays described herein, though other assays are feasible. This activity connotes at least one characterizing activity of MIRRF. The complete protein as well as any fragment thereof theft retains the above-described biological activity is contemplated herein. Such fragments can be generated, for example, by mechanical or chemical disruption of the complete protein or, as another example, they can be recombinant proteins obtained by cloning nucleic acids encoding the polypeptide in an expression system capable of producing the protein or fragments thereof. The activity of such fragments can be determined utilizing the methods taught below in the Examples.

By "a nucleic acid that codes for the protein" is meant both single-stranded and double-stranded nucleic acids. Such term also includes any unique portion of the nucleic acid. By "unique portion" is contemplated a nucleotide sequence that substantially does not occur on known nucleic acids.

The nucleic acid coding for the protein of MIRRF can be readily determined by any of several techniques standard in the art (see, for example Sambrook et at., *Molecular Cloning: A Laboratory Manual*, 2nd Ed., Cold Spring Harbor Laboratory, Cold Spring Harbor, N.Y. (1989)). The known amino acid sequence, for example, in human, SEQ ID NO.1, and in mouse, SEQ ID NO. 2, can be used to deduce the nucleotide sequence of the portion of the gene corresponding to the known amino acids (here, the amino terminus). Because of the redundancy of the genetic code, more than one nucleic acid sequence can be deduced. Probes or primers, for example, containing these sequences, or portions thereof, can be made. If desired, probes or primers can be chosen from regions of less redundancy and/or a mixture of probes can be used. One method to isolate and determine the nucleic acid encoding MIRRF, for example, involves using primers to amplify DNA from monocytes and the amplified DNA can then be sequenced. Such amplification methods are known to those skilled in the art.

Alternatively, a labeled probe can be utilized to screen a gene library. One method can employ a "subtractive hybridization" with both a cDNA library from monocytes stimulated with insulin and a cDNA library from monocytes unstimulated with insulin, such that MIRRF would be preferentially expressed in the stimulated cells. Positive clones can be isolated and purified and the sequence of the DNA insert of the clone determined, for example, by the dideoxynucleotide chain-termination method. Of particular use is the screening of a library constructed in an expression vector (such as λgt11 and others) so that the protein encoded by the isolated MIRFF clone can be expressed. An expression vector library can be screened utilizing a labeled nucleic acid probe or by immunological screening of in vitro translation products from the library clones (see Glover, D. M. ed. *DNA Cloning*, Vol. 1 (IRL Press, Oxford, (1985)). Once the proper clone is obtained and the protein expressed, such expressed protein can then be characterized, as by amino acid sequencing, bioassaying for reduction of insulin receptor binding and determining antigenic regions of the protein.

The term "nucleic acid which codes for" the MIRRF protein, as used herein, refers to the primary nucleotide sequence of a gene encoding the amino acid sequence of MIRFF, as exemplified by the partial human and mouse amino acid sequences listed in SEQ ID NO. 1 and SEQ ID NO. 2, respectively. The gene may or may not be expressed in the native host. If it is not expressed in the native host, it may still be capable of being manipulated through recombinant techniques to effect expression in a foreign host. The term refers both to the precise nucleotide sequence of a gene found in a mammalian host as well as modified genes which still code for a MIRRF polypeptide having biological activity. The gene may exist as a single contiguous sequence or may, because of intervening sequences and the like, exist as two or more discontinuous sequences, which are nonetheless transcribed in vivo to ultimately effect the biosynthesis of a protein substantially equivalent to that defined as MIRRF, above. Such modifications may be deliberate, resulting from, for example, site directed mutations. Such modifications may be neutral, in which case they result in redundant codons specifying the native amino acid sequence or in such modifications which may in fact result in a change in amino acid sequence which has either no effect, or only an insignificant effect on MIRRF activity. Such modifications may include point mutations, deletions or insertions.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "nucleic acid that codes for" the MIRRF protein may thus refer to one or more genes within a particular individual. Moreover, certain differences in nucleotide sequences may exist between individual organisms, which are called alleles. Such allelic differences may or may not result in differences in amino acid sequence of the encoded polypeptide while still encoding a protein with MIRRF activity.

A "host" refers to a cell or an organism that is capable of expressing the MIRRF protein encoded by the nucleic acid coding for MIRRF. Such hosts can be readily determined by methods known to those skilled in the art, and can include bacteria, yeast, and mammalian cells, for example. The choice of host can be correlated and guided by the choice of vector, as discussed below. It is understood that such terms refer not only to a particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A molecule comprising a vector and the nucleic acid of the present invention is also provided. Also contemplated is a molecule having a vector and a unique portion of the nucleic acid. The molecule of the invention can be in a host capable of expressing the antigen. Methods for producing such molecules and placing them within a host are described in (Sambrook et al., *Molecular Cloning: A Laboratory Manual*, 2nd Ed., Cold Spring Harbor Laboratory, Cold Spring Harbor, N.Y. (1989)).

There are numerous *E. coli* expression vectors known to one of ordinary skill in the art useful for the expression of the antigen. Other microbial hosts suitable for use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication), and if necessary an amino terminal methionine can be provided by insertion of a Met codon 5' and in-frame with the antigen.

Additionally, yeast expression can be used. For example, the *Saccharomyces cerevisiae* pre-pro-alpha-factor leader region (encoded by the MFα-1 gene) is routinely used to direct protein secretion from yeast (Brake et al., 1984). The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal.

Alternative vectors for the expression of protein in mammalian cells, those similar to those developed for the expression of human gamma-interferon, tissue plasminogen activator, clotting Factor VIII, hepatitis B virus surface antigen, protease NexinI, and eosinophil major basic protein, can be employed. Further, the vector can include CMV promoter sequences and a polyadenylation signal available for expression of inserted DNAs in mammalian cells (such as COS7).

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

An antibody selectively reactive with an antigenic portion of the protein is also provided. The antibodies can be selectively reactive with a unique epitope of the antigen or they can also react with epitopes of other organisms. The term "reactive" means capable of binding or otherwise associating nonrandomly with an antigen "Selectively reactive" as used herein describes an antibody or other ligand that is specifically reactive, that is, one that does not cross react substantially with any antigen other than the one specified, in this case, monocyte-derived insulin receptor regulatory factor, such that the intended antigen can be detected. Antibodies can be made by well-known methods, such as described in Harlow and Lane, *Antibodies; A Laboratory Manual*, Cold Spring Harbor Laboratory, Cold Spring Harbor, N.Y., (1988). Briefly, purified MIRRF protein, or an antigenic fragment thereof is injected into an animal in an mount and in intervals sufficient to elicit an immune response. Polyclonal antibodies can be purified directly by passing serum collected from the animal through a column to which non-MIRRF proteins prepared from the same expression system without MIRRF have been bound. Monoclonal antibodies can also be produced by obtaining spleen cells from the animal. The cells are then fused with an immortal cell line and screened for antibody secretion. The antibodies can be used to screen DNA clone libraries for cells secreting the antigen. Those positive clones can then be sequenced if desired (see, for example, Kelly et al., *Bio/Technology* 10:163-167, (1992) and Bebbington et al., *Bio/Technology* 10:169-175, (1992)).

Also provided is a method of reducing insulin receptor binding on T-lymphocytes in a subject by increasing the amount of MIRRF in the subject. Such reduction can be accomplished by, for example, administering the protein to the subject, or by causing the subject to produce an increased amount of MIRRF, as by causing an increase in transcription of the gene encoding MIRFF or an increase in translation of MIRRF mRNA. An increase in transcription can be effected, for example, by providing a MIRRF transcription enhancing factor or by inhibiting a MIRRF transcription down-regulating factor. An increase in translation can be effected, for example, by an increased production of MIRFF mRNA or by increasing the stability of the MIRFF mRNA molecule.

Additionally, provided is a method of inhibiting the biological activity of MIRRF. Such intuition can be accomplished by administering a ligand capable of binding to a biologically active portion of the protein. A ligand can be any molecule that can be specifically bound to a protein; a typical example is an antibody, as described above.

The aforementioned methods involve administration of compound such as the MIRRF protein, antibodies to MIRRF, and other ligands, to a subject. The compounds may be administered by means well known to those of skill in the art for administration of proteins. Such means, and the proper dosages, are exemplified by the administration of such proteins as insulin, interleukin-2 and immunoglobulins, for example, as are known to those of skill in the art. Parenteral administration is typically preferred. The exact amount of such compounds required will vary from subject to subject, depending on the species, age, weight and general condition of the subject, the severity of the disease that is being treated, the particular compound used, its mode of administration, and the like. Thus, it is not possible to specify an exact amount. However, an appropriate amount may be determined by one of ordinary skill in the art using only routine experimentation given the teachings herein. Generally, dosage will approximate that which is typical for the administration of cytokines, as is known to those of skill in the art.

The compositions will preferably be in unit dosage form suitable for single administration of a precise dosage and may include an effective amount of the selected compound in combination with a pharmaceutically acceptable carrier, for example, saline, and in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. Actual methods of preparing such dosage forms are known, or will be apparent, to those skilled in this art; for example, see *Remington's Pharmaceutical Sciences* (45).

Parenteral administration is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

This invention provides two examples of the newly discovered monocyte derived insulin receptor regulatory factor, human and mouse. The invention contemplates the homologous proteins in other organisms, as can be readily detected by any of several means known to those of skill in the art, such as by screening gene libraries of other organisms with a labeled probe derived from the nucleotide sequence of the human or mouse MIRRF-encoding gene and expression of the thusly cloned new gene. Alternatively, antibodies to the mouse or human protein can be produced and used to isolate MIRRF protein from a protein extract from another organism.

The present invention is more particularly described in the following examples which are intended as illustrative only since numerous modifications and variations therein will be apparent to those skilled in the art.

Throughout this application, various publications are referenced. The disclosures of these publications in their entireties are hereby incorporated by reference into this application in order to more fully describe the state of the art to which this invention pertains.

EXAMPLES

Cell Culture: mouse cell line

In order to approach isolation and purification of the T-lymphocyte insulin receptor regulatory substance derived from insulin-incubated monocytes, it was necessary to find a monocyte-macrophage culture cell line which synthesized the regulatory material at high concentration as discerned by bioassay analysis of conditioned medium. A murine line, P388D$_1$, derived from the DBAf2 strain was found to have the characteristics necessary for use as our starting point (ATCC Accession Number: TIB 63). This cell line has been characterized as a monocyte-macrophage cell line as it is esterase positive, secretes Interleukin-1, has phagocytic capability, bears Class II molecules, is devoid of cytoplasmic or membrane bound immunoglobulin, and lacks surface CD3, CD11, or CD12 (9). Initially, subcultures of this cell line at $10^6$/ml in RPMI 1640 (Gibco Co; Stanton Island, N.Y.) buffered with 10 mM HEPES and enriched with 5% (v/v) insulin-deplete fetal calf serum, hereafter called enriched medium, were incubated with and without $10^{-6}$M insulin in a total volume of 3 ml in a 6 well plastic micro-culture plate (Costar, Inc.; Cambridge, Mass.) for 24 hours at 37° C. in 5% CO$_2$ and air. At the completion of the incubation, the subcultures were extensively washed to remove incubating insulin. Fresh enriched, insulin-deplete medium was added to the cell lines and incubation was continued for a second 24 hours in the absence of any additional monocyte stimulus after the wash step. At this point conditioned medium was collected.

Cell Culture: Human cell line

A human monocyte cell line, THP-1 (ATCC Accession No. TIB 202), was selected as it is characterized as esterase positive, having Fc and C3b receptors, lacking surface and cytoplasmic immunoglobulins, and having phagocytic capability. Culture of THP-1 was conducted identically to that of P338D$_1$, described above, and at the conclusion of the culture steps, conditioned medium was collected.

Collection of Conditioned Medium

Twenty-five liters of conditioned medium were collected from P388D$_1$ or THP-1 insulin incubated cells. To accomplish this task the cell culture was sub-cultured and expanded into individual flasks of 150 ml volume (Corning Glass Works; Corning, N.Y.) of enriched medium for a total of 6 passages before stimulation of the culture by insulin to produce factor. At each additional passage and expansion in the face of insulin stimulation, the presence of the T-lymphocyte insulin receptor regulatory factor (MIRRF) was assessed by the standard bioassay detection system. Cells were passed on only if such activity was present. At this juncture, maintaining an approximate cell concentration of $2 \times 10^6$ P388D$_1$ or THP-1 cells/ml, enriched medium was discarded and a fresh aliquot of 150 ml of enriched medium was added which contained a final concentration of insulin of $10^{-6}$M for the cultures from which conditioned medium was to be collected for further purification. Simultaneously a control group of the same cells were maintained in the absence of insulin incubation from which conditioned medium was collected in order to compare the constituents of the insulin incubated monocyte cell line medium to those that had been un-stimulated by the hormone. After 24 h incubation at 37° C. in 5% CO$_2$ and air the insulin containing medium was discarded, cells were extensively washed ($3 \times$ in PBS devoid of calcium and magnesium) and were recultured with 150 ml of enriched, insulin-deplete medium with no further additional insulin. After a second 24 h incubation, all of the conditioned medium was collected, a small aliquot tested at frequent intervals for bioassayable material, and the bulk pooled and stored at $-70°$ C. for later concentration and further purification. In no instance was an active receptor regulatory factor present in the "negative" control studies and in every instance the factor had to be present in the insulin incubated lines for retention.

Bioassay For MIRRF Detection

Presence of the putative T-lymphocyte insulin receptor regulatory material was assessed by a standard radioligand binding bioassay described below and previously (1,10-13). In brief, the bioassay is based on the capacity of conditioned medium in a dose response fashion to alter the vigor of T-lymphocyte insulin receptor synthesis after lectin activation. For these studies, human T-lymphocytes responding to phytohemagglutinin-P (PHA-P) constituted the index system for the detection of putative monocyte-derived insulin receptor regulatory substance (MIRRF). Populations of lymphocytes highly enriched for T-lymphocytes (greater than 95% as determined by cytofluorographic analysis of T-lymphocyte specific surface markers) were obtained from peripheral blood of consenting human volunteers by leukopheresis, an experiment conducted under the aegis of the Institutional Review Board of Vanderbilt University. Cell mixtures from leukopheresis were further separated by ficoll-Hypaque density gradient separation (sp. grav=1.077). The mononuclear cells were recovered from the interface and further separated by nylon wool filtration as previously described (1,13). These nylon wool non-adherent, T-lymphocyte enriched cell populations were placed at $10^7$/ml in enriched medium to which was added 1 ml of the enriched medium containing various dilutions of conditioned medium from the insulin incubated and washed P388D$_1$ cell line (murine) or THP-1 cell line (human) along with a final concentration of PHA-P of 3.75/μg/ml (Difco; Detroit, Mich.). Culture was continued for 48 hours at 37° C. in 5% CO$_2$ and air after which T-lymphocytes were extensively washed and recovered for analysis of the insulin receptor by a radioligand binding assay.

Radioligand Insulin Receptor Assay

T-lymphocyte insulin receptor measurements are standard in this laboratory, the technique of which has been described and characterized (1,10–13). For these studies, the index cell of interest was a lectin transformed human T-lymphocyte obtained as described above. The human T-lymphocytes were placed at $1 \times 10^7$/ml in binding buffer (25 mM Na acetate, 2.4 mM KCl, 0.81 mM MgSO$_4$, 0.81 mM EDTA, 10 mM mannitol, 10 mM HEPES, 0.1% (V$N$) 5× recrystallized bovine serum albumin, pH. 7.8) after completion of the PHA-P stimulated tissue cultures in the presence or absence of putative monocyte-derived factor (MIRRF). For each replicate, 200 μl of T-lymphocytes were placed in 12×75 mm borosilicate tubes exposed to 10 ng/ml [$^{125}$I]-iodoinsulin (80–120 μCi/μg; New England Nuclear; Boston, Mass.). Equilibrium binding conditions were established by incubation at 24° C. for 45 minutes in the presence or absence of 100-fold excess unlabelled, single peak insulin as previously described (13). This concentration of radioligand was chosen as it provides binding in association binding isotherms at this temperature and time on the rapid upslope of the isotherm at a concentration near the affinity constant (Kd). Cells are collected by centrifugation through oil and bound radiolabeled insulin determined, for example, by scintillation counting, as described in (13).

Purification of MIRRF

The 25 liters of conditioned medium obtained from the insulin incubated P388D$_1$ or THP-1 cultures as described above were thawed and concentrated to a final volume of 100 ml employing a hollow fiber diafiltration system using an Amicon Stir-cell with a YM10 diaflow membrane, under pressure (Amicon; Danvers, Mass.). This crude concentrate was tested for potential unique substances on 12% SDS-PAGE when compared to gels run from conditioned medium obtained in the absence of insulin incubation. SDS-PAGE of this concentrate revealed a multiplicity of bands with a hint of an unique band found only in the insulin-incubated, monocyte-derived conditioned medium in the molecular mass range between 14–21 kDa. The 100 ml was further concentrated by the Amicon chamber with a YM30 filter followed by a YM5 filter to obtain material between 5 and 30 kDa. This crude extract was placed over a Sephadex G25-M/PD10 (PD10; Pharmacia, Inc.; Piscataway, N.J.) column to remove salt and phenyl red with the active bioassayable material collected in the void volume. 2.5 ml of concentrate was added to each column followed by wash with 5 ml of PBS and collection of active material in the void volume. This void volume was subjected to bioassay analysis to ensure the presence of MIRRF. The void volumes from 10 separate columns (total volume 25 ml) were further concentrated using a Centriprep 10 micro separation device based on our preliminary molecular weight analysis of the crude conditioned medium concentrate (Amicon Co.) giving a final volume of 5 ml.

The concentrated material from the G-25 columns were frozen and preserved at −70° C. for further purification by size exclusion chromatography in a fast pressure liquid chromatography system (FPLC). For each further separation, approximately 1 ml of the concentrate was thawed and separated at any one time placing 200 μl on each size exclusion column packed with Superose 12, a cross-linked allarose matrix with 10 μm bead size and column geometry of 10×300 min. Each column was equilibrated with 50 mM phosphate, 150 mM NaCl and eluted at the rate of 1.0 ml/min. Each fraction from the column was assessed for MIRRF by the standard radioligand binding assay as described above. The insulin incubated cell line chromatogram showed unique peaks not seen in the insulin-free cell line profile.

Unique peaks from the column present in the conditioned medium in the insulin incubated cell line which had MIRRF activity not found in the cell lines without insulin stimulation were further analyzed on 12% SDS-PAGE. Two to three unique bands are seen in the insulin-incubated monocyte medium that are not found in the negative control. The large unique peaks from the column containing the bioassay positive material and a large amount of serum albumin were pooled and concentrated once again with the centripep 10.

These concentrated unique fractions were further purified by chromatofocusing using the anion exchange system Mono Q HR 10/10 (Pharmacia) in a column geometry of 10 mm×100 mm length upon which was placed 1 ml of sample eluted with a linear gradient of 0–1M NaCl at a flow rate of 1 ml/min. With a starting buffer of 20 mM potassium phosphate, MIRRF was eluted using a linear increase of salt concentration up to 100% 1M NaCl (FIG. 4, Panel A). The negative insulin control cell-line was subjected to the same conditions (FIG. 4, Panel B). Unique peaks can be seen only in the conditioned medium from the insulin-incubated monocyte cell line. Again, fractions from the insulin stimulated cell line containing bioassayable MIRRF not present in the control line without insulin incubation were reserved and analyzed by 12% SDS-PAGE. Unique proteins between 14 and 21 kDa were clearly visible suggesting that purification of MIRRF was near to homogeneity after this step but serum albumin contamination continued to be present.

To complete the purification profile, the active fractions from the anion exchange chromatofocusing gel were subjected to high pressure liquid chromatography (HPLC) using a size exclusion column (Protein PAK, SW300, Waters Chromatography Division of Millipore Corp.; Milford, Mass.) using two columns in series injecting 500 μl samples and eluting with a buffer containing 20 mM Na acetate and 150 mM NaCl, pH 6.0 at 1 ml/min. 1 ml fractions were collected. Unique peaks in the insulin incubated monocyte cell line chromatogram had high biologic activity when tested. A concentrate of this active MIRRF fraction was subjected to SDS-PAGE electrophoresis.

Because a small amount of contaminating albumin remained which might make transblotting for sequence analysis more difficult, a final chromatography step after concentration of HPLC active fractions was performed using a series of columns containing Econo-pat blue packed with g-gel blue coupled to an Econo-pat P6 column packed with Biogel P6 (Bio-Rad; Richmond, Calif.). This final step was performed in order to give an unique band on SDS-PAGE, between the molecular weight range of 14 and 21 kDa, from which transblotting was completed.

The HPLC peak with biologically active material was then separated on 12% SDS-PAGE and electrophoretically transferred to a PVDF membrane for 45 min at 100 volts using a 0.025M Tris-glycine buffer, pH=8.3. After the proteins were transferred, the PVDF membrane was stained with Coomassie Blue for 5 min, destained for 10 min, and air-dried overnight. Amino acid sequence analysis was performed in the lab of Dr. Audree Fowler of University of California, Los Angeles.

A second aliquot was also separated on 12% SDS-PAGE and then electroeluted (Schleicher and Schuell Elutrap; Nashua, N.H.) with Tris(25 mM)-glycine(192 mM), pH=8.5 at 200 volts, overnight at 4° C. The electroeluted sample was removed, filter (0.2 22μ) sterilized and tested to show it is biologically active material in the standard MIRRF bioassay described above.

Amino Acid Sequence of Human MIRRF

Sequence analysis was performed on the amino terminus of the isolated human MIRRF. Amino acids were obtained (DSVGAGEPKLY - - - DVD P/K SAT/I V/E S) [SEQ ID NO. 1]. This amino acid sequence shows 35% homology to pre-albumin. A comparison of this amino acid sequence to other known protein sequences in a protein data bank indicates that it is unique.

Amino Acid Sequence of Murine MIRRF

Sequence analysis was performed on the amino terminus of the isolated murine MIRRF, obtaining the first 26 amino acids (XGVGAGEPKLPLMVKDLDAVRXXPAA) [SEQ ID NO. 2] which is 60% homologous to the very large transthyretin molecule. To demonstrate that this sequence is the biologically relevant molecule, the HPLC peak was separated on SDS-PAGE gels and then electroeluted. A 1:100 dilution of the final purified electroeluted material reduced insulin receptor binding on activated T cells by 60%.

Although the obtained sequence has some homology to transthyretin, it is still around 40% variant and comes from a very much smaller molecule than transthyretin providing evidence for its uniqueness. That electroeluted peptide from the final gel used for sequence at a 1:100 dilution could reduce insulin receptor binding on T-lymphocytes by 60% proves that the sequenced material is the biologically relevant molecule we have sought to characterize and purify.

Although the present process has been described with reference to specific details of certain embodiments thereof, it is not intended that such details should be regarded as limitations upon the scope of the invention except as and to the extent that they are included in the accompanying claims.

REFERENCES

1. Helderman, J. H., Strom, T. B. (1977) The emergence of insulin receptors upon alloimmune cells in the rat. J Clin Invest 59:338-344.
2. Helderman, J. H., Strom, T. B. (1978) The specific insulin binding site on T and B lymphocytes: A marker of cell activation. Nature (London) 274:62-63.
3. Helderman, J. H., Reynolds, T. C., Strom, T. B. (1978) The insulin receptor as a universal marker of activated lymphocytes. Eur J Immunol 8:589-595.
4. Helderman, J. H., Strom, T. B., Dupuy-d'Angeac A (1979) A close relationship between cytotoxic T lymphocytes generated in the mixed lymphocyte culture and insulin receptor bearing lymphocytes: enrichment by density gradient centrifugation. Cell Immunol 46:247-258.
5. Strom, T. B., Helderman, J. H. (1980) Comparison of ligand specific rat allosensitized lymphocyte insulin receptors as assessed in binding and functional (lymphocyte mediated cytotoxicity) assays. Cell Immunol 53:382-388.
6. Helderman, J. H. (1981) The role of insulin in the intermediary metabolism of the activated thymic derived lymphocyte. J Clin Invest 67:1636-1642.
7. Helderman, J. H., Gruchalla, R., Edwards, L. E. (1984) Effect of insulin and transferrin in the maintenance of the activated state of the T-lymphocyte induced by alloantigen. Diabetalog 27:99-101.
8. Helderman, J. H., Ayuso, R., Rosenstock, J., Raskin, P. (1987) Human monocyte-T-lymphocyte interaction for the regulation of lymphocyte insulin receptor display. J Clin Invest 79:566-571.
9. Karen, H. S., Handwerger, B. S., Wonderlich, J. R. (1975) Identification of macrophage-like characteristics in a cultured murine tumor line. J Immunol 114:894-897.
10. Helderman, J. H., Raskin, P. (1980) The T-lymphocyte insulin receptor in diabetes and obesity: An intrinsic binding defect. Diabetes 29:551-557.
11. Helderman, J. H., Pietri, A., Raskin, P. (1983 In vitro control of T-lymphocyte insulin receptors by in vivo modulation of insulin. Diabetes 32:712-717.
12. Helderman, J. H. (1983) T-cell cooperation for the genesis of B-cell insulin receptors. J Immunol 131:644-650.
13. Helderman, J. H., Strom, T. B. (1979) Role of protein and RNA synthesis in the development of insulin binding sites on activated thymus-derived lymphocytes. J Biol Chem 254:7203-7207.
14. Spira, G. P., Aman, P., Koiden, N., Ludin, G., Klein, G., Hall, K. (1981) Cell-surface immunoglobulin and insulin receptor expression in an EBV-negative lymphoma cell line and its EBV-converted sublines. J Immunol 126:122-126.
15. Koffler, M., Raskin, P., Womble, D., Helderman, J. H. (1991) Immunobiologic consequence of regulation of the insulin receptor on alloactivated lymphocytes in normal and obese subjects. Diabetes 40:364-370.
16. Ercolani, L., Brown, T. S., Ginsberg, B. H. (1984) Tunicamycin blocks the emergence of insulin receptors on activated T-lymphocytes. Metab Clin Exp 33:309-316.
17. Helderman, J. H. (1984) Acute regulation of human lymphocyte insulin receptors analysis by the glucose clamp. J Clin Invest 74:1428-1435.
18. Matsushima, K., Larsen, C. G., DuBois, G. C., Oppenheim, J. J. (1989) Purification and characterization of a novel monocyte chemotatic and activating factor produced by a human myelomonocytic cell line. J Exp Med 169:1485-1490.
19. Matsushima, K., Morishita, K., Yoshimura, T., Lavu, S., Kobayashi, Y., Lew, W., Appella, E., Kung, H. F., Leonard, E. H., Oppenheim, J. J. (1988) Molecular cloning of a human monocyte-derived neutrophil chemotactic factor (MDNCF) and the induction of (MDNCF) and the induction of MDNCF mRNA by interleukin 1 and tumor necrosis factor. J Exp Med 167:1883-1893.

20. Arai, K. I., Lee, F., Miyajima, A., Miyatake, S., Arai, N., Yokota, T. (1990) Cytokines: coordinators of immune and inflammatory responses. Ann Rev Biochem. 59:783–836.
21. Gubler, V., Chua, A. O., Schoenhaut, D. S., Dwyer, C. M., McComas, M., Motyka, R., Nabavi, N., Wolitzky, A. G., Quinn, D. M., Familletti, P. C., Gately, M. K. (1991) Coexpression of two distinct genes is required to generate secreted bioactive cytotoxin lymphocyte maturation factor. Proc Natl Acad Sci 88:4143–4147.

What is claimed is:

1. A purified protein comprising the amino acid sequence set forth in SEQ ID NO 1 and having the biological activity of reducing insulin receptor binding on T-lymphocytes.

2. A purified protein consisting of the amino acids in the sequence set forth in SEQ ID NO:1 and having the biological activity of reducing insulin receptor binding on T-lymphocytes.

* * * * *